(12) United States Patent
Hu et al.

(10) Patent No.: US 11,766,199 B2
(45) Date of Patent: Sep. 26, 2023

(54) OXIMETER

(71) Applicant: CONTEC MEDICAL SYSTEMS CO., LTD., Qinhuangdao (CN)

(72) Inventors: Kun Hu, Qinhuangdao (CN); Yunlong Xu, Qinhuangdao (CN); Jinling Zhang, Qinhuangdao (CN); Yatao Zhao, Qinhuangdao (CN); Zhichao Song, Qinhuangdao (CN); Di Wu, Qinhuangdao (CN); Bohua Yan, Qinhuangdao (CN)

(73) Assignee: CONTEC MEDICAL SYSTEMS CO., LTD., Qinhuangdao (CN)

( * ) Notice: Subject to any disclaimer, the term of this patent is extended or adjusted under 35 U.S.C. 154(b) by 61 days.

(21) Appl. No.: 16/755,054

(22) PCT Filed: Aug. 15, 2019

(86) PCT No.: PCT/CN2019/100831
§ 371 (c)(1),
(2) Date: Apr. 9, 2020

(87) PCT Pub. No.: WO2020/035038
PCT Pub. Date: Feb. 20, 2020

(65) Prior Publication Data
US 2022/0007977 A1  Jan. 13, 2022

(30) Foreign Application Priority Data
Aug. 16, 2018 (CN) .......................... 201810932700.2

(51) Int. Cl.
*A61B 5/1455* (2006.01)
*A61B 5/00* (2006.01)

(52) U.S. Cl.
CPC ........ *A61B 5/14552* (2013.01); *A61B 5/0093* (2013.01); *A61B 5/6824* (2013.01);
(Continued)

(58) Field of Classification Search
CPC . A61B 5/14552; A61B 5/0093; A61B 5/6824; A61B 5/6826; A61B 5/742;
(Continued)

(56) References Cited

U.S. PATENT DOCUMENTS 4,859,056 A * 8/1989 Prosser .............. A61B 5/14551
356/41
2002/0161291 A1 * 10/2002 Kianl ................... A61B 5/0002
600/324

(Continued)

FOREIGN PATENT DOCUMENTS

CN        103750830 A     4/2014
CN        104188663 A     12/2014
(Continued)

OTHER PUBLICATIONS

PCT International Search Report, Application No. PCT/CN2019/100831, dated Nov. 13, 2019, 6 pages: with English translation.
(Continued)

*Primary Examiner* — Eric F Winakur
*Assistant Examiner* — Abid A Mustansir
(74) *Attorney, Agent, or Firm* — Armstrong Teasdale LLP (57) ABSTRACT

The disclosure relates to an oximeter, including a blood oxygen collecting unit that has a first light emitting unit emitting a red light, a second light emitting unit emitting an infrared light, and a light receiving sensor receiving the red light emitted by the first light emitting unit and not absorbed by a human body and the infrared light emitted by the second light emitting unit and not absorbed by the human body, and converting them into an electrical signal, a storage unit that stores measurement data and/or a power-on startup screen, the power-on startup screen including the last measurement result of a blood oxygen saturation and/or previous measurement results of the blood oxygen saturation, a
(Continued)

power-on button that is for power-on startup, a microprocessor that calculates a blood oxygen saturation of the human body based on the electrical signal detected by the light receiving sensor.

15 Claims, 5 Drawing Sheets (52) U.S. Cl.
CPC ............ *A61B 5/6826* (2013.01); *A61B 5/742* (2013.01); *A61B 2560/0214* (2013.01); *A61B 2560/04* (2013.01); *A61B 2562/0238* (2013.01)

(58) Field of Classification Search
CPC ........ A61B 2560/0214; A61B 2560/04; A61B 2562/0238; A61B 5/145
See application file for complete search history.

(56) References Cited

U.S. PATENT DOCUMENTS

| | | | | |
|---|---|---|---|---|
| 2008/0243393 | A1* | 10/2008 | Yamamoto | A61B 5/4818 702/19 |
| 2008/0281168 | A1* | 11/2008 | Gibson | G16H 40/63 600/301 |
| 2011/0080294 | A1 | 4/2011 | Tanishima et al. | |
| 2011/0218406 | A1 | 9/2011 | Hussain | |
| 2013/0079601 | A1* | 3/2013 | Addison | A61B 5/7221 600/301 |
| 2014/0135631 | A1* | 5/2014 | Brumback | A61B 5/11 600/479 |
| 2014/0180595 | A1* | 6/2014 | Brumback | G06F 1/1694 702/19 |
| 2014/0275903 | A1 | 9/2014 | Elder et al. | |
| 2014/0357966 | A1* | 12/2014 | Al-Ali | A61B 5/318 600/301 |
| 2016/0247378 | A1* | 8/2016 | Baczuk | H04W 4/80 |
| 2018/0085058 | A1 | 3/2018 | Chakravarthi et al. | |
| 2020/0335211 | A1* | 10/2020 | Gopalakrishnan | G16H 40/20 |

FOREIGN PATENT DOCUMENTS

| | | |
|---|---|---|
| CN | 104246506 A | 12/2014 |
| CN | 104932672 A | 9/2015 |

OTHER PUBLICATIONS

PCT Written Opinion, Application No. PCT/CN2019/100831, dated Nov. 13, 2019, 9 pages.: with English translation of relevant part.
European Extended Search Report, Application No. 19850487.0, dated Apr. 28, 2022, 9 pps.

* cited by examiner

OXIMETER

CROSS REFERENCE TO RELATED APPLICATIONS

This patent application is a National Stage Entry of PCT/CN2019/100831 filed on Aug. 15, 2019, which claims the benefit and priority of Chinese Patent Application No. 201810932700.2 filed on Aug. 16, 2018, the disclosures of which are incorporated by reference herein in their entirety as part of the present application.

BACKGROUND

Embodiments of the present disclosure relate to an oximeter, and more particularly to an oximeter that displays the measurement history at power-on.

Oximeter is used to detect the blood oxygen saturation of a human body, and the blood oxygen saturation is one of the important physiological parameters reflecting human body health. More and more patients are measuring their health status by monitoring blood oxygen saturation.

In the prior art, when an oximeter is powered on, it either displays a black screen without performing any processing, or displays a LOGO or an advertisement.

Specifically, Patent Document 1 (CN201611198799.5) relates to a power-on display processing method based on a mobile terminal and a system. When the mobile terminal is powered off, a power-on display file is downloaded from the network, and the power-on display file includes an advertisement file. When it is detected that the power-on key of the mobile terminal is pressed in a power-off state, the display control right of the system is prohibited, the power-on display file is acquired for playing, and meanwhile the power-on process is performed. When the playing is finished, the display control right is returned to the system.

BRIEF DESCRIPTION

In view of the prior art mentioned above, the present disclosure provides an oximeter that can display the last measurement result of a blood oxygen saturation and/or previous measurement results of the blood oxygen saturation at power-on, which allows the user to view the trend of the last measurement result or the previous measurement results, and to understand his own body parameter levels and/or comparison of parameters before and after physical exercise as well as before and after oxygen inhalation. Specifically, the disclosure provides the following technical solution.

An oximeter is provided, including a blood oxygen collecting unit that has a first light emitting unit, a second light emitting unit, and a light receiving sensor, the first light emitting unit emitting a red light, the second light emitting unit emitting an infrared light, and the light receiving sensor receiving the red light emitted by the first light emitting unit and not absorbed by a human body and the infrared light emitted by the second light emitting unit and not absorbed by the human body, and converting them into an electrical signal, a storage unit that stores measurement data and/or a power-on startup screen, the power-on startup screen including the last measurement result of a blood oxygen saturation and/or previous measurement results of the blood oxygen saturation, a power-on button that is used for power-on startup; a microprocessor that calculates a blood oxygen saturation of the human body based on the electrical signal detected by the light receiving sensor, and after the power-on button is pressed, generates a power-on startup screen based on the measurement data stored in the storage unit or reads a power-on startup screen stored by the storage unit, and sends the power-on startup screen to a display unit, and a display unit that displays the power-on startup screen after power-on.

Alternatively, the power-on startup screen includes a trend graph of the previous measurement results of the blood oxygen saturation.

Alternatively, the power-on startup screen includes an average value of the previous measurement results of the blood oxygen saturation.

Alternatively, the power-on startup screen processing unit updates the power-on startup screen based on a measurement result of the blood oxygen saturation this time, and sends the updated power-on startup screen to the storage unit.

Alternatively, a collecting screen is displayed in the display unit after the time for displaying the power-on startup screen reaches a predetermined time.

Alternatively, the oximeter further includes an input unit that sets the display content of the power-on startup screen.

Alternatively, the input unit sets at least one of the predetermined time, a first threshold value, a second threshold value, a third threshold value, a first frequency, a second frequency, a third frequency, a first duration, a second duration, and a third duration.

Alternatively, the oximeter further includes an I/O interface for charging a battery unit and/or connecting to other blood oxygen collecting devices.

Alternatively, the oximeter further includes a wireless communication unit.

Alternatively, the oximeter is a finger clip oximeter, a wrist oximeter, or a head-mounted oximeter. A blood oxygen collecting unit of the finger clip oximeter includes a concave blood oxygen collecting port in which a finger can be put, and the first light emitting unit, the second light emitting unit, and the light receiving sensor are set in the concave blood oxygen collecting port. A blood oxygen collecting unit of the wrist oximeter includes a blood oxygen finger clip set outside a casing, and the blood oxygen finger clip is connected with an interface set at the casing.

BRIEF DESCRIPTION OF THE DRAWINGS

In order to describe the technical solutions of the embodiments of the present disclosure more clearly, drawings of the embodiments will be briefly described below. Obviously, the drawings described below merely relate to some embodiments of the present disclosure, other than restrictions to the present disclosure.

DETAILED DESCRIPTION

In order to clarify the technical solution and advantages of the embodiments of the present disclosure, the technical solutions of the embodiments of the present disclosure will be clearly and completely described in conjunction with the drawings of the embodiments of the present disclosure below. Obviously, the embodiments to be described refer to a part of the embodiments of the present disclosure, other than all of the embodiments. On the basis of the embodiments of the present disclosure to be described, all other embodiments those skilled in the art obtain requiring no inventive effort also belong to the scope protected by the present disclosure.

Figure 1:
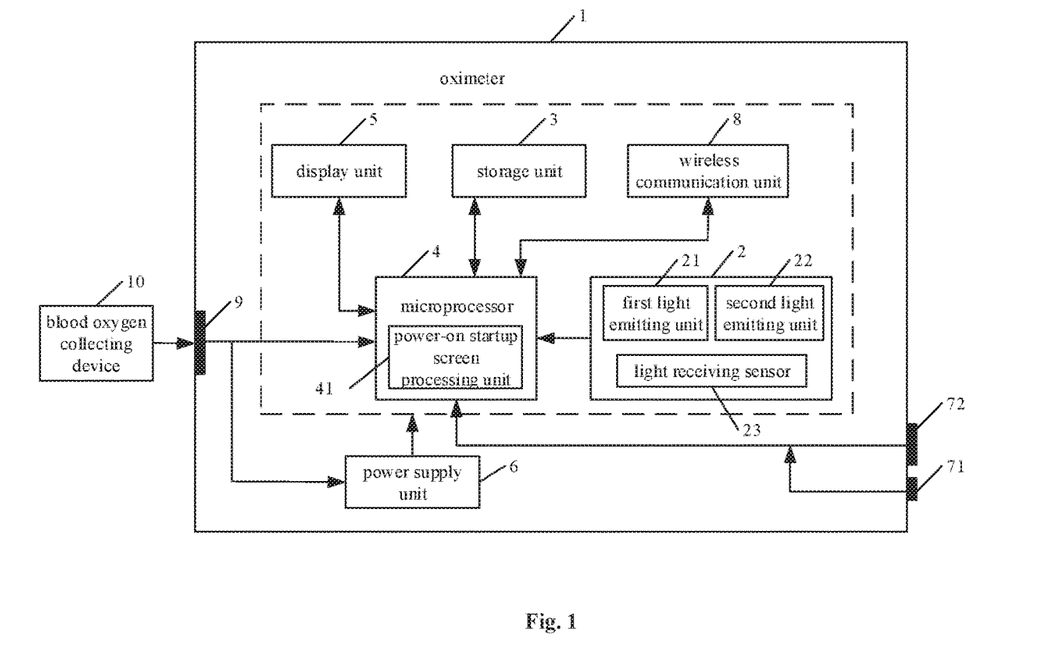
FIG. 1 is a schematic structural diagram of an oximeter according to an embodiment of the present disclosure.

FIG. 1 is a schematic structural diagram of an oximeter according to an embodiment of the present disclosure.

As shown in FIG. 1, the oximeter 1 of the present embodiment includes a blood oxygen collecting unit 2 that has a first light emitting unit 21, a second light emitting unit 22, and a light receiving sensor 23, the first light emitting unit 21 emitting a red light, the second light emitting unit 22 emitting an infrared light, and the light receiving sensor 23 receiving the red light emitted by the first light emitting unit 21 and not absorbed by a human body and the infrared light emitted by the second light emitting unit 22 and not absorbed by the human body, and converting them into an electrical signal, a storage unit 3 that stores a power-on startup screen, the power-on startup screen including the last measurement result of a blood oxygen saturation and/or previous measurement results of the blood oxygen saturation, a power-on button 71 that is used for power-on startup, a microprocessor 4 that calculates a blood oxygen saturation of the human body based on the electrical signal detected by the light receiving sensor 23, and after the power-on button is pressed, generates a power-on startup screen based on the measurement data stored in the storage unit or reads a power-on startup screen stored by the storage unit, and sends the power-on startup screen to a display unit 5, and a display unit 5 that displays the power-on startup screen after power-on.

Furthermore, the microprocessor 4 may also include a power-on startup screen processing unit 41 that, after the power-on button is pressed, generates a power-on startup screen based on the measurement data stored in the storage unit or reads a power-on startup screen stored by the storage unit, and sends the power-on startup screen to a display unit 5.

The oximeter 1 of the present embodiment may be a portable oximeter such as a finger clip oximeter, a wrist oximeter, or a head-mounted oximeter well-known in the art, and it may further be a table oximeter used in hospital, and the present disclosure has no limitation on this.

When the oximeter 1 of the present embodiment is used for the first time, there is no previous measurement result of the blood oxygen saturation to be displayed at power-on, and a collecting screen is directly displayed in the oximeter after power-on.

The oximeter 1 of the present embodiment may obtain the blood oxygen saturation by any method well-known in the art. An example is specifically described below, but the present embodiment is not limited to this.

For instance, if the measurement time is less than 1 second, the collected data is discarded, and if the measurement time is more than 1 second, the data is recorded. The stability of the blood oxygen data collected in 10 seconds is mainly judged according to the stability of the waveform and the stability of the data. If the data is stable, the data of the previous 10 seconds would be replaced, and if the data is unstable, it would be discarded.

When the oximeter is used again after the first use, the power-on startup screen is displayed at power-on.

The power-on startup screen may include the last measurement result of the blood oxygen saturation and/or previous measurement results of the blood oxygen saturation. Furthermore, the power-on startup screen may include a trend graph of the previous measurement results of the blood oxygen saturation. Moreover, the power-on startup screen may include an average value of the previous measurement results of the blood oxygen saturation.

Figure 2:
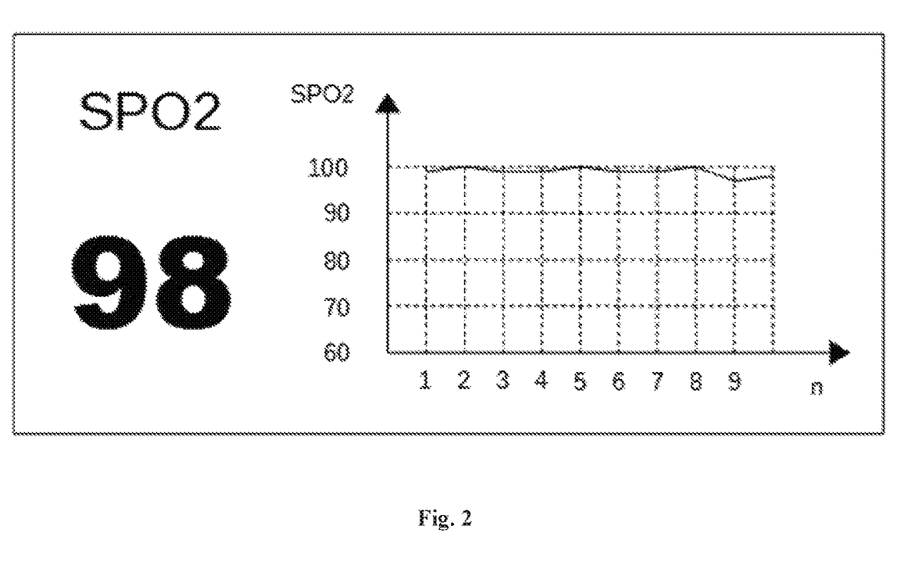
FIG. 2 is an example of a power-on startup screen of an oximeter according to an embodiment of the present disclosure.

FIG. 2 is an example of a power-on startup screen of an oximeter according to an embodiment of the present disclosure. As shown in FIG. 2, the left side of the power-on startup screen is the last measurement result of the blood oxygen saturation, and the right side is the trend graph of the previous measurement results of the blood oxygen saturation. In addition, the last measurement result of the blood oxygen saturation on the left side may also be replaced with an average value of the previous measurement results of the blood oxygen saturation. In the example shown in FIG. 2, a trend graph of the blood oxygen saturation in the previous 10 times is displayed, but the number of times included in the trend graph can be arbitrarily set.

In the present embodiment, the method for obtaining the trend graph of blood oxygen saturation in previous times by the power-on startup screen processing unit 41 is, for example, using the blood oxygen saturation measured each time as the vertical axis and the number of times as the horizontal axis to create a trend graph. In the present embodiment, the trend graph is indicated by a wavy line, but it may also be indicated in other forms well-known in the art.

Figure 3:
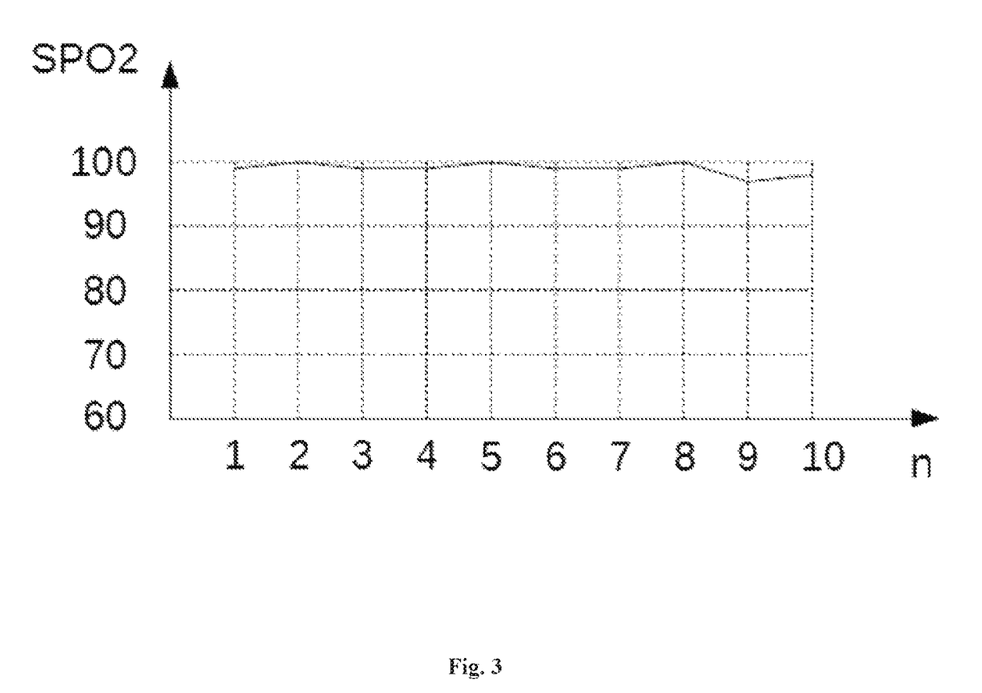
FIG. 3 is another example of a power-on startup of an oximeter according to an embodiment of the present disclosure.

FIG. 3 is another example of a power-on startup of an oximeter according to an embodiment of the present disclosure. As shown in FIG. 3, only a trend graph of the blood oxygen saturation of the previous 10 times is displayed, while the blood oxygen saturation of the last time is not displayed.

Furthermore, in addition to the blood oxygen saturation, the power-on startup screen may further include data such as a pulse rate and a PI value, and the present disclosure has no limitation on this.

In the present embodiment, the power-on startup screen processing unit 41 updates the power-on startup screen based on a measurement result of the blood oxygen saturation this time, and sends the updated power-on startup screen to the storage unit 3 for displaying at the next power-on.

Furthermore, the display unit 5 displays the power-on startup screen for a predetermined time, for example, 10 seconds, and a collecting screen is entered after the displaying time reaches the predetermined time.

The oximeter 1 of the present embodiment may display the last measurement result of a blood oxygen saturation and/or previous measurement results of the blood oxygen saturation at power-on, which allows the user to view the last measurement result or the trend of the previous measurement results, and to understand his own body parameter levels and/or comparison of parameters before and after physical exercise as well as before and after oxygen inhalation.

The blood oxygen collecting unit 2 of the present embodiment has a first light emitting unit 21, a second light emitting unit 22, and a light receiving sensor 23. The first light emitting unit 21 and the second light emitting unit 22 are, for instance, LEDs, which are light emitting diodes. The first light emitting unit 21 emits a red light of 660 nm for instance, and the second light emitting unit 22 emits an infrared light of 905 nm, 910 nm, or 940 nm for instance. The light receiving sensor 23 is, for instance, a photosensitive sensor, receiving lights emitted by the first light emitting unit 21 and the second light emitting unit 22 and not absorbed by the human body, and converting them into an electrical signal.

In a specific working process, the first light emitting unit 21 and the second light emitting unit 22 may alternately emit light. In this way, the light receiving sensor 23 may alternately receive the red light emitted by the first light emitting unit 21 and not absorbed by the human body and the infrared light emitted by the second light emitting unit 22 and not absorbed by the human body. In addition, the light receiving sensor 23 may include two sensors, each of which independently receives the lights emitted by the first light emitting unit 21 and the second light emitting unit 22 and not absorbed by the human body. In this way, the first light emitting unit 21 and the second light emitting unit 22 do not need to emit light alternately, but may emit light continuously.

Furthermore, the blood oxygen collecting unit 2 may also include three or more light emitting units to improve the collection accuracy.

In a case where the oximeter 1 is a finger clip oximeter, a blood oxygen collecting unit 2 includes a concave blood oxygen collecting port in which a finger can be put, and the first light emitting unit 21, the second light emitting unit 22, and the light receiving sensor 23 are set in the concave blood oxygen collecting port.

In a case where the oximeter 1 is a wrist oximeter, a blood oxygen collecting unit 2 includes a blood oxygen finger clip set outside a casing, and the blood oxygen finger clip is connected with an interface set at the casing. In addition, the blood oxygen collecting unit 2 of the wrist oximeter may also be set inside the casing.

Figure 6:
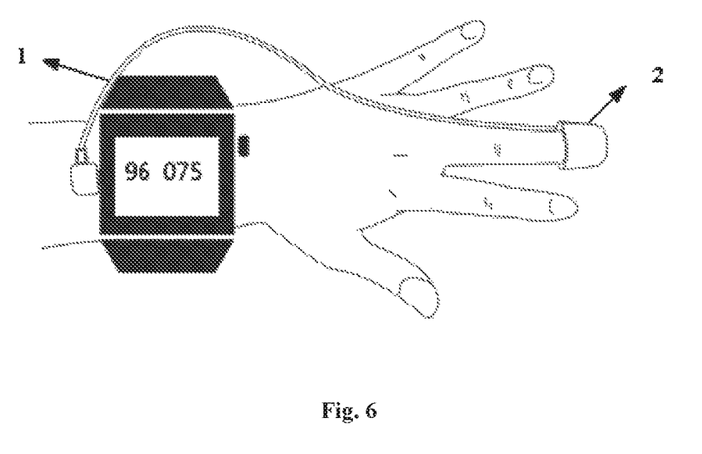
FIG. 6 is an example of a wrist oximeter according to an embodiment of the present disclosure.

Specifically, FIG. 6 is an example of a wrist oximeter according to an embodiment of the present disclosure. As shown in FIG. 6, the blood oxygen collecting unit 2 of the wrist oximeter 1, i.e., a blood oxygen finger clip, is set outside, and the blood oxygen finger clip is set to be connected with an interface set at the casing.

In a case where the oximeter 1 is a head-mounted oximeter, a blood oxygen collecting unit 2 may also be set outside or inside the casing like a wrist oximeter. When being set outside, the blood oxygen collecting unit 2 is connected through an interface set on the casing.

The blood oxygen collecting unit 2 sends the collected electrical signal to the microprocessor 4 which calculates the blood oxygen saturation of the human body based on the received electrical signal. The method for the microprocessor 4 to calculate the blood oxygen saturation based on the electrical signal collected by the blood oxygen collecting unit 2 may be any method well-known in the art, and is not described in detail in the present disclosure.

The display unit 5 of the present embodiment, after data is collected, may display any one or more of a bar graph, a blood oxygen value, a pulse rate value, a PI value, and a waveform graph, and the present disclosure has no limitation on this.

Figure 4:
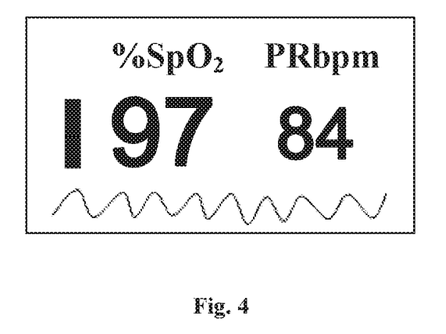
FIG. 4 is an example of a detection result screen displayed by a display unit of an oximeter according to an embodiment of the present disclosure.
Figure 5:
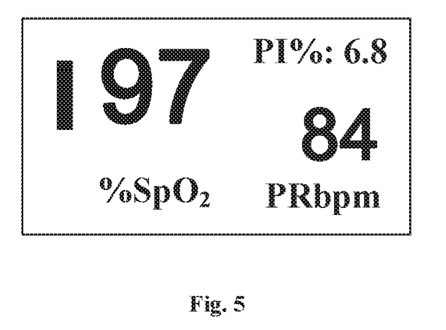
FIG. 5 is another example of a detection result screen displayed by a display unit of an oximeter according to an embodiment of the present disclosure.

Specifically, FIG. 4 is an example of a screen displayed by a display unit of an oximeter according to an embodiment of the present disclosure. FIG. 5 is another example of a screen displayed by a display unit of an oximeter according to an embodiment of the present disclosure. As shown in FIG. 4, a bar graph, a blood oxygen value, a pulse rate value, and a waveform graph are displayed on the display unit 5. As shown in FIG. 5, a bar graph, a blood oxygen value, a pulse rate value, and a PI value are displayed on the display unit 5.

The oximeter 1 of the present embodiment may further include an input unit 72, and the display content of the power-on startup screen is set through the input unit 72, that is, it is set that the last measurement result of the blood oxygen saturation, or a trend graph of the previous measurement results of the blood oxygen saturation is displayed in the power-on startup screen, or both are displayed at the same time, or an average value of the previous blood oxygen saturation is displayed instead of the last blood oxygen saturation.

Furthermore, at least one of the predetermined time, the first threshold value, the second threshold value, the third threshold value, the first frequency, the second frequency, the third frequency, the first duration, the second duration, and the third duration may also be set by the input unit 72.

The input unit 72 is, for instance, a button. The button may be one or more elastic cylindrical buttons set in the casing and protruding from the surface of the casing. By pressing the button, the oximeter can be powered on and off, the function can be set, and the threshold values, frequencies, and durations can be set. In a case where the power on/off function may be implemented by the input unit 72, there is no need to additionally set a power-on button 71, that is, the power-on button 71 is a part of the input unit 72. In other words, the input unit 72 and the power-on button 71 may be combined into one input unit.

Furthermore, instead of setting the input unit 72, the input function may be set at the display unit 5. For instance, the display unit 5 has a touch control function, and the user implements the input control described above through the display unit 5.

Furthermore, the oximeter 1 of the present embodiment may further include a wireless communication unit 8 that receives a parameter setting instruction from a mobile terminal and sends display screen to the mobile terminal. The user can communicate with the wireless communication unit 8 through the mobile terminal, control the oximeter 1, or transmit the data detected by the oximeter 1 to the mobile terminal.

Furthermore, the oximeter 1 of the present embodiment may further include a power supply unit 6. The battery unit 6 may be a dry battery or a rechargeable battery, and supplies power to various components of the oximeter 1.

Furthermore, the oximeter 1 of the present embodiment may further include an I/O interface 9 which is, for instance, a USB interface. In a case where the battery unit 6 is a rechargeable battery, the battery unit 6 may be charged through the I/O interface 9.

Furthermore, the I/O interface 9 may be used as a collecting interface for externally connecting to other blood oxygen collecting devices 10, so that it can be connected to a traditional finger clip or finger sleeve blood oxygen collecting device, which is suitable for nighttime or long-term monitoring.

Furthermore, after the power-on button is pressed, the microprocessor 4 queries whether measurement data is stored in the storage unit, it is displayed if it exists, and a normal measurement screen is entered if not.

Furthermore, a power-on startup screen related to the user is generated by the microprocessor based on user information and sent to the display unit. The user information may include user information manually selected by the user and/or physiological information of the user detected via a sensor.

Specifically, before the stored data is displayed, the corresponding user data information may be manually selected, or the user may be identified based on the user's physiological information. The physiological information may be an electrical signal converted and output by the light receiving sensor, and may be information such as amplitude information, period information of the output signal, especially information related to pulse wave data. The pulse wave data may be characteristic value information of a waveform, and may also be other information such as pulse rate information that can be obtained from a pulse wave. Corresponding stored data is searched according to the information. The stored data includes user non-physiologically relevant data and physiologically relevant data. The non-physiological data includes, but is not limited to, age, gender, weight, and the like, and the physiologically relevant data includes, but is not limited to, set threshold values, test durations, test data, and statistical results of measurement data, and the like. After a certain period of time, the default setting is adopted when no matching information is found, and the user-related information is updated and stored. Since the user needs to be identified before each normal test is performed, after each measurement is finished, the user can turn off the device or the device exits the normal test.

Furthermore, it is possible that the user only wants to view the test results. At this time, in order to save power, no test is performed when the stored data is displayed.

Furthermore, before the predetermined time is reached, in a case where it is detected that the display of the measurement data is finished or it is judged that the output of the light receiving sensor is a valid signal, a collecting screen is entered by the microprocessor.

When a frequency of a frequency signal output by the light receiving sensor is within a predetermined frequency range, or when a voltage of a voltage signal output by the light receiving sensor is within a predetermined voltage range, it is judged by the microprocessor that output of the light receiving sensor is a valid signal.

In a case where the signal output by the light receiving sensor is a frequency signal, when light is emitted at a first-stage light emission intensity, it is detected whether the frequency of the frequency signal is greater than a first frequency, and if it is greater than the first frequency, the light emission intensity is reduced to a second-stage light emission intensity, when light is emitted at the second-stage light emission intensity, it is detected whether the frequency of the frequency signal is greater than the first frequency, and if it is greater than the first frequency, the light emission intensity is reduced to a third-stage light emission intensity, and when light is emitted at the third-stage light emission intensity, it is detected whether the frequency of the frequency signal is greater than the first frequency, and if it is greater than the first frequency, it is judged that the frequency signal is not a valid signal, and if it is smaller than or equal to the first frequency, it is judged that the frequency signal is a valid signal.

Specifically, it is judged whether the output of the light receiving sensor is a valid signal while displaying the test data, and when a valid signal is detected, a collecting screen is entered for testing, or when displaying of the stored data is finished, the collecting screen is entered, which speeds up the data measurement and display rate than the test is started after waiting for a fixed time Ti.

Judging of the valid signal is based on the following description, that is, the signal received by the light receiving sensor is a signal that is not absorbed by human body tissue, and the greater the degree of human body blood filling is, the smaller the intensity of the signal that is not absorbed by human body tissue is. A threshold value is set for judgment; for instance, when the electrical signal converted and output by the light receiving sensor is a frequency signal, it can be set that when the frequency signal is greater than a certain frequency range, it is judged that no human body tissue is detected, and then it is judged that the output at the time is not a valid signal; when the output electrical signal is a voltage signal, it can be set that when the voltage signal is greater than a certain voltage range, it is judged that no human body tissue is detected, and then it is judged that the output at the time is not a valid signal. Since there are differences in different human bodies or human body tissues, and the electrical signal is related to the light emission intensity. When the circumference of a human body tissue, e.g. a finger is small, the unabsorbed light signal will be much greater than that of a finger with a greater circumference, and the light intensity may be adjusted to adapt to different fingers to expand the range of use. For instance, when the output signal is a frequency signal, when the light is emitted at a first-stage light emission intensity, it is detected that the frequency of the sensor output signal is greater than 50 KHz, and the light emission intensity is reduced to a second-stage light emission intensity; then, it is judged whether the frequency is greater than 50 KHz, and if it is, the light emission intensity is reduced to a third-stage light emission intensity; further, it is judged whether the frequency is greater than 50 KHz, and if it is still, it is then judged that the frequency signal at the time is not a valid signal, otherwise it can be judged that the frequency signal at the time is a valid signal to adapt to different human body tissues.

Furthermore, as for when the normal measurement screen is entered, a fixed duration is generally set. In order to take displaying of different types of information into account, the fixed duration needs to be set based on the maximum duration. Further, in order to increase the rate of starting the measurement to reduce the waiting time of the user, it may be judged when the normal measurement screen can be entered, thereby speeding up the rate of entering the normal measurement screen and reducing unnecessary waiting time. Specifically, a screen of stored data is displayed after the device is woken up, and it is detected by the device whether the normal measurement screen can be entered in real time. After it is detected that the normal measurement screen can be entered, displaying of the stored data screen is stopped.

Specifically, detecting of whether the measurement screen can be entered is indicated by an accessibility sign. After the microprocessor detects the sign, displaying of the stored data is stopped and the normal measurement screen is entered. Furthermore, before judging whether the normal measurement screen can be entered, it includes when displaying the stored data, the microprocessor starts to receive the output signal of the light receiving sensor, and judges whether the signal is a valid signal, when the microprocessor detects that displaying of the stored data is finished and detects a valid signal, the normal measurement screen is immediately entered, or the output signal from the light receiving sensor is processed by the microprocessor; when the measurement data is obtained and the microprocessor detects that displaying of the stored data is finished and a valid signal is detected, the normal measurement screen is immediately entered, where the measurement data may be a blood oxygen saturation value or a pulse rate value. In order to prevent constant waiting when displaying of the stored data is finished but the microprocessor has never detected a valid signal or valid data, a default time period may be set. The timing starts at the same time when the device is woken up, and when the microprocessor detects that the measurement screen can be immediately entered or the timing time meets one of the conditions, the measurement screen is immediately entered.

Furthermore, the display space of the display unit is divided into a plurality of sub-spaces by the microprocessor based on a statistical result of the stored measurement data, and they are displayed in a manner that sizes of the sub-spaces and the statistical result are positively correlated. A smaller sub-space may be displayed in a vibrant color.

Specifically, the display mode is selected according to the type of the stored physiologically relevant data, wherein the type of data refers to the statistical results of the N data of the last N measurements (especially to obtaining a stored data each time) and the data of the N periods of time of the last N measurements. Since the device can be externally connected to a blood oxygen unit, when a segment of data needs to be measured, an external connected blood oxygen unit may be used, while the blood oxygen unit inside the device may be used when measuring data for a single time. When the displayed data is a plurality of data for a single time that are physiologically relevant, it may be displayed in a switching manner or in form of a trend graph, and when a statistical result of physiologically relevant data is displayed, it may be to use an area chart for displaying. The display space is divided into N sub-spaces according to the number N of segments, and sizes of the sub-spaces and the data statistical results are positively correlated. For instance, the stored data contains 3 segments of blood oxygen saturation data, and the values include 50 99%, 30 98%, 10 97%, and 10 96%, wherein the stored data contains 4 different values, the display space is divided into 4 sub-spaces, the number of data is 50+30+10+10=100, and the space is divided into 100 parts as a whole, wherein a sub-space with a value of 99% occupies 50% of the display space, a sub-space with a value of 98% occupies 30% of the display space, a sub-space with a value of 97% occupies 10% of the display space, and a sub-space with a value of 96% occupies 10% of the display space. Moreover, the corresponding numerical information is marked on each corresponding sub-space. The sub-spaces may be further labeled using different colors. For data with a small space ratio, a more vibrant color can be used for labeling. For instance, a sub-space of 10% is labeled using red, and that of 50% is labeled using green. The displaying based on the display area is easier for viewing the statistical result. After adding the color distinguishing marks, vibrant colors are used for a few possible abnormal data, which can more easily attract attention.

Furthermore, a part including data before an abnormality occurs and data immediately after an abnormality occurs, and a part including data at the end of an abnormality and data after the abnormality in the trend graph of the measurement results are intercepted by the microprocessor for displaying.

Specifically, there are special cases for displaying the trend graph of stored data. When the graph contains a large amount of data, especially after the number of data exceeds the number that can be displayed on one screen, it needs to switch to the next page to continue displaying the data. When a user wants to view a certain segment of data, he needs to select the data and switch the display, which is not easy to operate, especially when there is data exceeding the threshold value, users will pay attention to the trend of the data before and after the data exceeds the threshold. When there is abnormal data between normal data, especially when the continuous data of abnormal data exceeds one screen display, or when the data is repeatedly displayed more than one screen, it is more inconvenient to view the data, at the time, the following display mode may be used, that is, the data before the abnormal data and the data segment immediately when the abnormality are invoked for displaying, and at the same time the data segments after the abnormal data and the end of the abnormal data are invoked for displaying, and the intercepted two segments of data are displayed one above the other to facilitate comparison.

Furthermore, a collecting screen and a screen displaying the stored measurement data are displayed in the display unit in a switching manner at a predetermined frequency, or the stored measurement data is displayed in a sub-screen of the collecting screen. In the display unit, when there is data exceeding a threshold value in the stored measurement data, it may be displayed in a flickering manner.

Specifically, after the normal measurement screen is entered, the stored data is displayed in a sub-screen of the measurement screen or the stored data is displayed in a switching manner, so as to facilitate comparing and viewing the difference between the measurement data this time and the stored data. Displaying of the data in a switching manner solves the problem due to display space limitation. Moreover, when threshold value data is set and there is data exceeding the threshold value in the stored data, when the data is displayed, a flickering reminder is used to notice the abnormal information last time.

Although the oximeter according to the present disclosure has been described in detail through some exemplary embodiments, the above embodiments are not exhaustive. Those skilled in the art may implement various changes and modifications within the spirit and scope of the present disclosure. Therefore, the present disclosure is not limited to these embodiments, and the protection scope of the present disclosure is determined only by the appended claims.

What is claimed is:

1. An oximeter comprising:
   a blood oxygen collecting circuit that has a first light emitting circuit, a second light emitting circuit, and a light receiving sensor, the first light emitting circuit emitting a red light, the second light emitting circuit emitting an infrared light, and the light receiving sensor i) receiving the red light emitted by the first light emitting circuit and not absorbed by a human body and the infrared light emitted by the second light emitting circuit and not absorbed by the human body, and ii) converting the received light into an electrical signal;
   a storage circuit that stores measurement data and/or a power-on startup screen, the power-on startup screen including a last measurement result of a blood oxygen saturation and/or previous measurement results of the blood oxygen saturation;
   a power-on button that is used for power-on startup;
   a microprocessor that calculates a blood oxygen saturation of the human body based on the electrical signal converted by the light receiving sensor, and after the power-on button is pressed, generates the power-on startup screen based on the measurement data stored in the storage circuit or reads the power-on startup screen stored by the storage circuit, and sends the power-on startup screen to a display; and the display that displays the power-on startup screen which is generated by the microprocessor based on the measurement data of the blood oxygen saturation stored in the storage circuit or the power-on startup screen including the last measurement result of the blood oxygen saturation and/or the previous measurement results of the blood oxygen saturation which is stored in the storage circuit after power-on, wherein a display space of the display is divided into a plurality of sub-spaces by the microprocessor based on a statistical result of the stored measurement data, and wherein the plurality of sub-spaces are displayed such that sizes of the sub-spaces and the statistical result are positively correlated, wherein a smaller sub-space is displayed in a red color, wherein the plurality of sub-spaces are displayed by an area chart, and wherein the microprocessor intercepts a part including data before an abnormality occurs and data immediately after an abnormality occurs, and a part including data at the end of an abnormality and data after the abnormality in a trend graph of the previous measurement results for display, and the intercepted two segments of data are displayed one above the other.

2. The oximeter according to claim 1, wherein the power-on startup screen includes an average value of the previous measurement results of the blood oxygen saturation.

3. The oximeter according to claim 1, wherein the microprocessor updates the power-on startup screen based on a measurement result of the blood oxygen saturation, and sends the updated power-on startup screen to the storage circuit.

4. The oximeter according to claim 1, wherein a collecting screen is displayed on the display after a time for displaying the power-on startup screen reaches a predetermined time.

5. The oximeter according to claim 4, wherein before the predetermined time is reached, in a case where it is detected that displaying of the measurement data is completed or it is judged that output of the light receiving sensor is a valid signal, the collecting screen is entered by the microprocessor.

6. The oximeter according to claim 5, wherein the microprocessor, when a frequency of a frequency signal output by the light receiving sensor is within a predetermined frequency range, or when a voltage of a voltage signal output by the light receiving sensor is within a predetermined voltage range, judges that the output of the light receiving sensor is a valid signal.

7. The oximeter according to claim 5, wherein
the signal output by the light receiving sensor is a frequency signal,
when light is emitted at a first-stage light emission intensity, it is detected whether a frequency of the frequency signal is greater than a first frequency, and if the frequency of the frequency signal is greater than the first frequency, a light emission intensity is reduced to a second-stage light emission intensity,
when light is emitted at the second-stage light emission intensity, it is detected whether the frequency of the frequency signal is greater than the first frequency, and if the frequency of the frequency signal is greater than the first frequency, the light emission intensity is reduced to a third-stage light emission intensity, and
when light is emitted at the third-stage light emission intensity, it is detected whether the frequency of the frequency signal is greater than the first frequency, and if the frequency of the frequency signal is greater than the first frequency, it is judged that the frequency signal is not a valid signal, and if the frequency of the frequency signal is smaller than or equal to the first frequency, it is judged that the frequency signal is a valid signal.

8. The oximeter according to claim 1, further comprising an input circuit that sets display content of the power-on startup screen.

9. The oximeter according to claim 1, further comprising an I/O interface for charging a battery circuit and/or connecting to other blood oxygen collecting devices.

10. The oximeter according to claim 1, further comprising a wireless communication circuit that receives a parameter setting instruction from a mobile terminal and sends a display screen to the mobile terminal.

11. The oximeter according to claim 1, wherein the oximeter is a finger clip oximeter, a wrist oximeter, or a head-mounted oximeter, wherein a blood oxygen collecting circuit of the finger clip oximeter comprises a concave blood oxygen collecting port in which a finger can be put, wherein the first light emitting circuit, the second light emitting circuit, and the light receiving sensor are set in the concave blood oxygen collecting port, wherein a blood oxygen collecting circuit of the wrist oximeter comprises a blood oxygen finger clip set outside a casing, and wherein the blood oxygen finger clip is connected with an interface set at the casing.

12. The oximeter according to claim 1, wherein the microprocessor, based on user information, generates the power-on startup screen related to a user and sends it to the display.

13. The oximeter according to claim 12, wherein the user information includes user information manually selected by a user and/or physiological information of the user detected via a sensor.

14. The oximeter according to claim 1, wherein the display displays a collecting screen and a screen displaying the stored measurement data in a switching manner at a predetermined frequency, or displays the stored measurement data in a sub-screen of the collecting screen.

15. The oximeter according to claim 14, wherein the display, when there is data exceeding a threshold value in the stored measurement data, displays in a flickering manner.

* * * * *